United States Patent [19]
Pang et al.

[11] Patent Number: 5,681,854
[45] Date of Patent: Oct. 28, 1997

[54] USE OF ALIPHATIC CARBOXYLIC ACID DERIVATIVES IN OPHTHALMIC DISORDERS

[75] Inventors: Iok-Hou Pang, Grand Prairie; Michael A. Kapin, Arlington, both of Tex.

[73] Assignee: Alcon Laboratories, Inc., Fort Worth, Tex.

[21] Appl. No.: 563,315

[22] Filed: Nov. 22, 1995

[51] Int. Cl.$^6$ .................................................. A61K 31/19
[52] U.S. Cl. .......................................... 514/557; 514/912
[58] Field of Search ................................. 514/557, 912

[56] References Cited

U.S. PATENT DOCUMENTS

| | | | |
|---|---|---|---|
| 5,049,586 | 9/1991 | Ortega et al. | 514/557 |
| 5,169,642 | 12/1992 | Brinker et al. | 424/488 |

OTHER PUBLICATIONS

Elmazar, et al., *J. Pharm. Sci.*, "Anticonvulsant and Neurotoxic Activities of Twelve Analogues of Valproic Acid," 82(12): 1255–58, 1993.

Chapman, et al., "Mechanism of anticonvulsant action of valproate," *Progress in Neurobiology*, 19:315–359 (1982).

Czuczwar, et al., "Antagonism of N-methyl-D,L-aspartic acid-induced convulsions by antiepileptic drugs and other agents," *European Journal of Pharmacology*, 108:273–280 (1985).

Zeise, et al., "Valproate suppresses N-methyl-D-aspartate-evoked, transient depolarizations in the rat neocortex in vitro," *Brian Research*, 544:345–348 (1991).

Kapetanovic, et al., "Effects of pharmacological manipulations on basal and newly synthesized levels of GABA, glutamate, aspartate and glutamine in mouse brain cortex," *Biochemical Pharmacology*, 37(23):4445–4449 (1988).

Crowder, et al., "Common anticonvulsants inhibit calcium uptake and amino acid neurotransmitter release in vitro," *Epilepsia*, 28(4):378–382 (1987).

Slater, et al., "Sodium valproate increases potassium conductance in aplysia neurons," *Epilepsia*, 19:379–384 (1978).

Hackman, et at., "The presynaptic effects of valproic acid in the isolated frog spinal cord," *Brain Research*, 220:269–285 (1981).

Buchhalter, et al., "Effects of valproic acid in mammalian neurons," *Neurology*, 36:259–262 (1986).

Dreyer, et al., "A proposed role for excitatory amino acids in glaucoma visual loss," *Investigative Ophthalmology and Visual Science*, 34(suppl): 1504 (1993).

Shimada, et al., "Differences in ischemia–induced accumulation of amino acids in the cat cortex," *Stroke*, 21(10):1445–1451 (1990).

Drejer, et al., "Cellular origin of ischemia–induced glutamate release from brain tissue in vivo and in vitro," *Journal of Neurochemistry*, 45(1): 145–151 (1985).

Benveniste, et al., "Elevation of the extracellular concentrations of glutamate and aspartate in rat hippocampus during transient cerebral ischemia monitored by intracerebral microdialysis," *Journal of Neurochemistry*, 43(5): 1369–1374 (1984).

Beal, "Mechanisms of excitotoxicity in neurologic diseases," *FASEB Journal*, 6:3338–3344 (1992).

Choi, "Excitotoxic cell death," *Journal of Neurobiology*, 23(9):1261–1276 (1992).

Sattayasai, et al., "Morphology of quisqualate–induced neurotoxicity in the chicken retina," *Investigative Ophthalmology and Visual Science*, 28(1):106–117 (1987).

Tung, et al., "A quantitative analysis of the effects of excitatory neurotoxins on retinal ganglion cells in the chick," *Visual Neuroscience*, 4:217–223 (1990).

Sisk, et al., "Histological changes in the inner retina of albino rats following intravitreal injection of monosodium L–glutamate," *Graefe's Archives of Clinical and Experimental Ophthalmology*, 223:250–258 (1985).

Siliprandi, et al., "N–methyl–D–aspartate–induced neurotoxicity in the adult rat retina," *Visual Neuroscience*, 8:567–573 (1992).

Reif-Lehrer, et al., "Effects of monosodium glutamate on chick embryo retina in culture," *Investigative Ophthalmology and Visual Science*, 14(2):114–124 (1975).

David, et al., "Involvement of excitatory neurotransmitters in the damage produced in chick embryo retinas by anoxia and extracellular high potassium," *Experimental Eye Research*, 46:657–662 (1988).

Sucher, et al., "N-Methyl-D-aspartate antagonists prevent kainate neurotoxicity in rat retinal ganglion cells in vitro," *Journal of Neuroscience*, 11(4):966–971 (1991); and.

Dreyer, et al., "Greater sensitivity of larger retinal ganglion cells to NMDA –mediated cell death," *Neuroreport*, 5(5):629–631 (1994).

*Primary Examiner*—Zohreh Fay
*Attorney, Agent, or Firm*—Sally Yeager

[57] ABSTRACT

The use of certain aliphatic carboxylic acid derivatives to treat persons suffering from retinal or optic nerve head damage is disclosed.

12 Claims, No Drawings

USE OF ALIPHATIC CARBOXYLIC ACID DERIVATIVES IN OPHTHALMIC DISORDERS

The present invention is directed to the use of aliphatic carboxylic acid derivatives for the prevention and/or treatment of persons suffering from ophthalmic disorders, such as retinal or optic nerve head damage due to glaucoma, ischemia, hypoxia, edema, or trauma.

BACKGROUND OF THE INVENTION

Valproic acid, also known as 2-propylpentanoic acid, 2-propylvaleric acid or dipropylacetic acid, is an anticonvulsant. Its sodium salt, sodium valproate is available under the names Depakene Capsules® or Depakene Syrup® (Abbott) for the treatment of persons with epilepsy. A related compound, divalproex sodium or sodium hydrogen his (2-propylpentanoate), which is a stable coordination compound comprised of sodium valproate and valproic acid in a 1:1 molar relationship, is also available under the names Depakote Sprinkle Capsules® or Depakote Tablets® (Abbott) also for the treatment of persons with epilepsy.

Sodium valproate has been shown to antagonize convulsions induced by N-methyl-D-aspartate (NMDA) (Chapman, et al., "Mechanism of anticonvulsant action of valproate," *Progress in Neurobiology*, 19: 315–359 (1982); Czuczwar, et al., "Antagonism of N-methyl-D,L-aspartic acid-induced convulsions by antiepileptic drugs and other agents," *European Journal of Pharmacology*, 108: 273–280 (1985)). It also directly suppresses NMDA-evoked transient depolarizations in the rat neocortex (Zeise, et at., "Valproate suppresses N-methyl-D-aspartate-evoked, transient depolarizations in the rat neocortex in vitro," *Brain Research*, 544: 345–348 (1991)).

Valproate has also been shown to decrease the content of excitatory amino acids in neuronal tissues. In rodents, acute intraperitoneal administration of valproate decreases the concentration of aspartate in the cortex by 13–21% and that in the whole brain by 11–48% (Chapman, et al., supra). Valproate decreases both basal and newly synthesized brain aspartate levels (Kapetanovic, et al., "Effects of pharmacological manipulations on basal and newly synthesized levels of GABA, glutamate, aspartate and glutamine in mouse brain cortex," *Biochemical Pharmacology*, 37(23): 4445–4449 (1988)). In addition to decreasing the total content, this drag also reduces the veratridine-induced release of aspartate from rat cortical slices (Crowder, et al., "Common anticonvulsants inhibit calcium uptake and amino acid neurotransmitter release in vitro," *Epilepsia*, 28(4): 378–382 (1987)).

Furthermore, valproate has been shown to stabilize neuronal cell membrane potential. In studies with Aplysia neurons, valproate produced a concentration-dependent increase in membrane conductance to potassium ion (Slater, et al., "Sodium valproate increases potassium conductance in aplysia neurons," *Epilepsia*, 19: 379–384 (1978)). It attenuates the ability of excitatory amino acids to produce depolarizations and the subsequent excessive activation of neurons (Hackman, et al., "The presynaptic effects of valproic acid in the isolated frog spinal cord," *Brain Research*, 220: 269–285 (1981)). Application of therapeutic doses of valproate directly to a cortical neuron inhibits the generation of action potentials (Buchhalter, et al., "Effects of valproic acid in cultured mammalian neurons," *Neurology*, 36: 259–262 (1986)).

Finally, valproate has been shown to prolong survival of animals in anoxia, presumably due to its potential action in the reduction of neuronal metabolism and thereby diminish the neuron's need for oxygen (Chapman, et al., supra).

Many pathological changes in the retina and optic nerve head, such as damage related to glaucoma, ischemia, hypoxia, edema, or trauma are thought to be mediated, at least partly, by excitatory amino acids. In glaucomatous patients, glutamate concentration in the vitreous was found to increase significantly (Dreyer, et al., "A proposed role for excitatory amino acids in glaucoma visual loss," *Investigative Ophthalmology and Visual Science*, 34(suppl): 1504 (1993)). Furthermore, in conditions of cellular ischemia, hypoxia, or other stresses, excitatory amino acids were shown to be massively released (Shimada, et at., "Differences in ischemia-induced accumulation of amino acids in the cat cortex," *Stroke*, 21(10): 1445–1451 (1990)). Stresses, such as prolonged deprivation of oxygen and nutrients to neuronal tissues leads to cell membrane depolarization, which, in turn, increases synaptic glutamate release and reduces glutamate uptake, together resulting in a buildup of extracellular glumate (Drejer, et at., "Cellular origin of ischemia-induced glutamate release from brain tissue in vivo and in vitro," *Journal of Neurochemistry*, 45(1): 145–151 (1985); and Benveniste, et at., "Elevation of the extracellular concentrations of glytamate and aspartate in rat hippocampus during transient cerebral ischemia monitored by intracerebral microdialysis," *Journal of Neurochemistry*, 43 (5): 1369–1374 (1984)).

Excessive buildup of glutamate causes excessive stimulation of cells. Toxicity due to excessive stimulation by excitatory amino acids is referred to as excitotoxicity, which can cause lethal injury to the cells (Beat, "Mechanisms of excitotoxicity in neurologic diseases," *FASEB Journal*, 6: 3338–3344 (1992); and Choi, "Excitotoxic cell death," *Journal of Neurobiology*, 23(9): 1261–1276 (1992)). The same process of excitotoxicity in the retina has been studied. Toxicity to retina cells has been observed following intravitreal injection of excitatory amino acids, in vitro treatment of isolated retina with excitatory amino acids, or exogenously applied glutamate to retina/ganglion cells in culture. Some examples of references relating to this subject include:

Sattayasai, et al., "Morphology of quisqualate-induced neurotoxicity in the chicken retina," *Investigative Ophthalmology and Visual Science*, 28(1): 106–117 (1987);

Tung, et al., "A quantitative analysis of the effects of excitatory neurotoxins on retinaal ganglion cells in the chick,"*Visual Neuroscience*, 4: 217–223 (1990);

Sisk, et al., "Histological changes in the inner retina of albino rats following intravitreal injection of monosodium L-glutamate," *Graefe's Archives of Clinical and Experimental Ophthalmology*, 223: 250–258 (1985);

Siliprandi, et al., "N-methyl-D-aspartate-induced neurotoxicity in the adult rat retina," *Visual Neuroscience*, 8: 567–573 (1992);

Reif-Lehrer, et al., "Effects of monosodium glutamate on chick embryo retina in culture," *Investigative Ophthalmology and Visual Science*, 14(2): 114–124 (1975);

David, et al., "Involvement of excitatory neurotransmitters in the damage produced in chick embryo retinas by anoxia and extracellular high potassium," *Experimental Eye Research*, 46: 657–662 (1988);

Sucher, et al., "N-Methyl-D-aspartate antagonists prevent kainate neurotoxicity in rat retina/ganglion cells in vitro," *Journal of Neuroscience*, 11 (4): 966–971 ( 1991 ); and Dreyer, et at., "Greater sensitivity of larger retinal ganglion cells to NMDA—mediated cell death," *Neuroreport*, 5(5): 629–631 (1994).

SUMMARY OF THE INVENTION

The present invention is directed to the use of certain aliphatic carboxylic acid derivatives for the prevention and/or treatment of persons with ophthalmic disorders, such as retinal or optic nerve head damage due to glaucoma, ischemia, hypoxia, edema, or trauma.

DETAILED DESCRIPTION OF THE PREFERRED EMBODIMENTS

Compounds which are useful according to the present invention are aliphatic carboxylic acid derivatives having the following structure (hereinafter "Compounds"):

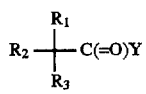

Y=OH; $NH_2$; $OC_{1-6}$ alkyl;

$R_1$=H; or $C_{1-3}$ alkyl;

$R_2$=H; $C_{1-4}$ alkyl; $C_{1-3}$ alkyl optionally substituted with OH; $CH_2CH_2COOH$; $C(=O)CH_2CH_3$;

$C_3$ alkenyl; or $C_3$ alkynyl;

$R_3$=$C_{1-10}$ alkyl; $C_3$ alkenyl; or $C_3$ alkynyl; $R_2$ and $R_3$ are joined together with carbon atoms to form a saturated six or seven-membered ring; or $(R_1R_2R_3)C$ taken together are

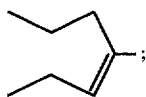

and pharmaceutically acceptable salts.

It is believed that the Compounds are useful in treating persons with ophthalmic disorders, such as, retinal or optic nerve head damage resulting in glaucoma, ischemia, edema, or trauma because of their ability in modulating the presynaptic release of excitatory amino acids and/or modulating the effects of excitatory amino acids on the postsynaptic receptor. The Compounds are also useful as prophylactics to prevent the occurrence of such diseases. The preferred Compound is valproate or its pharmaceutical equivalent, such as valproic acid, $(CH_3CH_2CH_2)_2CHCOOH$.

One or more of the Compounds are administered systemically, topically, by intraocular injection, intraocular perfusion, periocular injection, or retrobulbar injection. The Compounds are administered according to the routine discretion of a skilled clinician. When administered systemically, the daily dosage of Compound will range between about 0.5 and 60 milligrams per kilogram body weight per day (mg/kg/day), preferably between about 15 and 30 mg/kg/day.

The dosage range for local administration of the Compounds ranges between about 0.01 and 5.0% weight/volume percent (wt/vol. %), preferably between 0.1 and 1.0 wt/vol. %. Solutions, suspensions and other dosage forms adapted for topical, intraocular, periocular or retrobulbar administration are preferred.

The following Examples 1 and 2 are formulations useful for topical ocular application:

EXAMPLE 1

| Component | W/Vol % |
| --- | --- |
| Compound | 0.1 |
| Dibasic sodium phosphate | 0.2 |
| HPMC | 0.5 |
| Polysorbate 80 | 0.05 |
| Benzalkonium chloride | 0.01 |
| Sodium chloride | 0.75 |
| Edetate disodium | 0.01 |
| NaOH/HCl | pH 7.4 |
| Purified water | q.s. to 100% |

EXAMPLE 2

| Component | W/Vol % |
| --- | --- |
| Compound | 0.1 |
| Cremophor EL | 10 |
| Tromethamine | 0.12 |
| Boric acid | 0.3 |
| Mannitol | 4.6 |
| Edetate disodium | 0.1 |
| Benzalkonium chloride | 0.1 |
| NaOH/HCl | pH 7.4 |
| Purified water | q.s. to 100% |

EXAMPLE 3

The Compounds can be formulated in an ocular irrigating solution used during ophthalmic surgery to treat retinal or optic nerve head damage resulting from trauma due to injury or prevent damage resulting from the invasive nature of the surgery. These formulas are also useful for intraocular, periocular, or retrobulbar injection. Concentration of the Compound in the formulation is 0.01 to 5 wt./vol. %, preferably 0.1 to 1 wt./vol. %.

The following tablet formulation can be made pursuant to U.S. Pat. No. 5,049,586, incorporated herein by reference.

EXAMPLE 4

| Component | Weight % |
| --- | --- |
| Valproic acid | 60 |
| Magnesium oxide | 20 |
| Corn starch | 15 |
| Polyvinylpyrrolidone | 3 |
| Sodium carboxymethylcellulose | 1 |
| Magnesium stearate | 0.8 |

We claim:

1. A method for treating persons suffering from retinal or optic nerve head damage due to excitatory amino acids which comprises, administering a pharmaceutically effective amount of a compound of the structure:

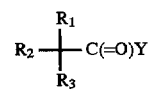

Y=OH; $NH_2$; $OC_{1-6}$ alkyl;

$R_1$=H; or $C_{1-3}$ alkyl;

$R_2$=H; $C_{1-4}$ alkyl; $C_{1-3}$ alkyl optionally substituted with OH; $CH_2CH_2COOH$; $C(=O)CH_2CH_3$;

$C_3$ alkenyl; or $C_3$ alkynyl;

$R_3=C_{1-10}$ alkyl; $C_3$ alkenyl; $C_3$ alkynyl; or $R_2$ and $R_3$ are joined together with carbon atoms to form a saturated six or seven-membered ring; or $(R_1R_2R_3)C$ taken together are

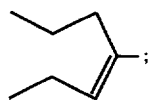

and pharmaceutically acceptable salts.

2. The method of claim 1 wherein the compound is valproate.

3. The method of claim 1 wherein the damage is a result of the person having glaucoma.

4. The method of claim 1 wherein the damage is a result of ischemia.

5. The method of claim 1 wherein the damage is a result of trauma.

6. The method of claim 1 wherein the damage is a result of edema.

7. The method of claim 1 wherein the compound is administered systemically.

8. The method of claim 1 wherein the compound is administered via intraocular injection.

9. The method of claim 1 wherein the compound is administered via periocular injection.

10. The method of claim 1 wherein the compound is administered via retrobulbar injection.

11. The method of claim 1 wherein the compound is administered topically.

12. The method of claim 1 wherein the compound is administered via a surgical irrigating solution.

* * * * *

UNITED STATES PATENT AND TRADEMARK OFFICE
CERTIFICATE OF CORRECTION

PATENT NO. : 5,681,854

DATED : October 28, 1997

INVENTOR(S) : Pang, et al.

It is certified that error appears in the above-identified patent and that said Letters Patent is hereby corrected as shown below:

Column 1, line 17, change "his" to *"bis"*

Column 1, line 46, change "drag" to "drug"

Signed and Sealed this

Tenth Day of March, 1998

Attest:

BRUCE LEHMAN

*Attesting Officer*      *Commissioner of Patents and Trademarks*